(12) United States Patent
Gerber et al.

(10) Patent No.: US 6,296,624 B1
(45) Date of Patent: Oct. 2, 2001

(54) BODY ACCESS SYSTEM

(76) Inventors: Allen Gerber, 42 Nutmeg Rd., Highfalls, NY (US) 12440; Lewis Gluck, 14 Fox Run, Wappingers Falls, NY (US) 12590; John G. Costa, P.O. Box 948, Highland, NY (US) 12528

( * ) Notice: Subject to any disclaimer, the term of this patent is extended or adjusted under 35 U.S.C. 154(b) by 0 days.

(21) Appl. No.: 09/192,084

(22) Filed: Nov. 14, 1998

Related U.S. Application Data

(63) Continuation-in-part of application No. 08/795,342, filed on Feb. 4, 1997, now Pat. No. 5,836,928.

(51) Int. Cl.$^7$ .................................................. A61M 5/178
(52) U.S. Cl. .............................. 604/164.11; 604/164.09; 604/272
(58) Field of Search .................... 604/104.01, 164.01, 604/164.11, 165.01, 165.02, 158, 152, 272, 164.09

(56) References Cited

U.S. PATENT DOCUMENTS 5,466,225 * 11/1995 Davis et al. ..................... 604/164.11

* cited by examiner

Primary Examiner—Anhtuan T. Nguyen
(74) Attorney, Agent, or Firm—John G. Costa

(57) ABSTRACT

A Body Access System for the collection of samples and the administration of fluids comprising means to prevent complete withdrawal of a needle stylet, means to dispose of needles and needle stylets provides for limited exposure to samples collected, needle sticks and stylet sticks.

6 Claims, 17 Drawing Sheets

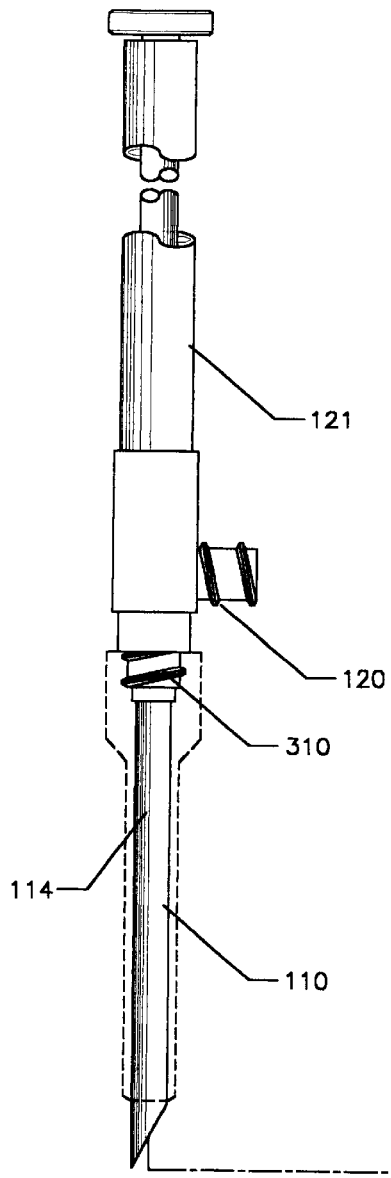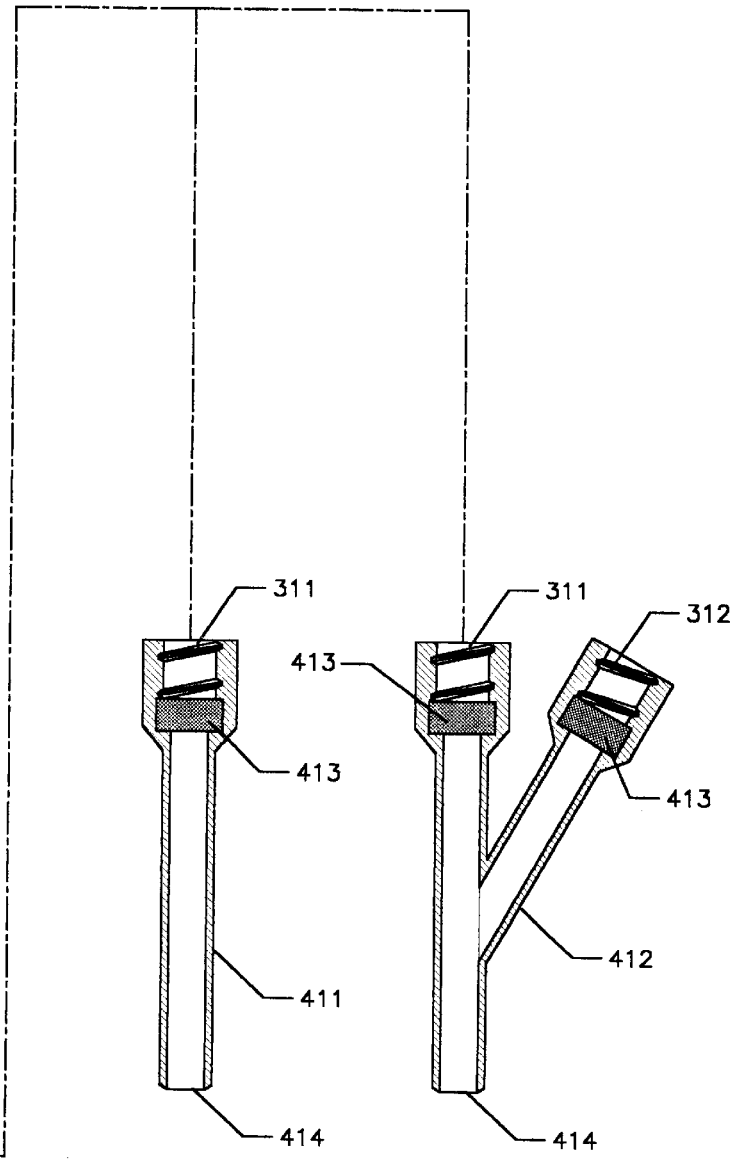
FIGURE 11a  FIGURE 11b  FIGURE 11c

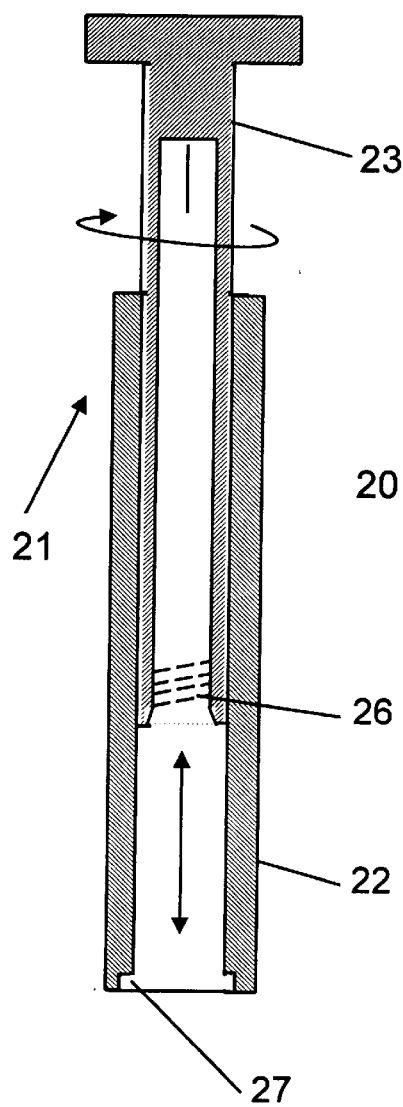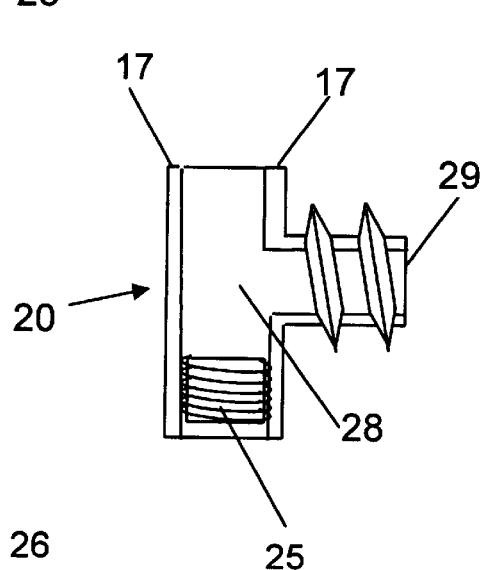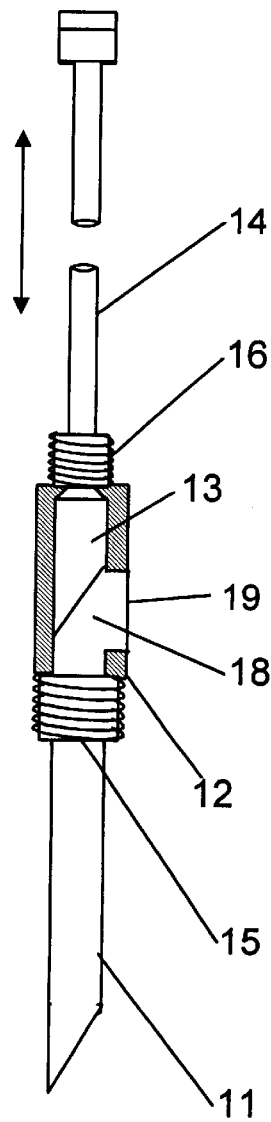
Figure 16a
Figure 16b
Figure 16c

BODY ACCESS SYSTEM

This is a continuation-in-part of U.S. patent application Ser. No. 08/795,342, filed Feb. 4, 1997, now U.S. Pat. No. 5,836,928.

FIELD OF THE INVENTION

The present invention relates to an improved body access system for the safe collection of samples and administration of fluids.

BACKGROUND OF THE INVENTION

The need for protection from exposure to needle sticks has been the impetus to the development of needle guards and needle protectors. Furthermore, an increased awareness of transmission of infections from exposure to body fluids or other samples has led to the development of improved means to limit exposure to samples collected.

An example of both a risk of sustaining a needle stick and also exposure to collected samples is the current procedure for the drawing of spinal fluid during a spinal tap. Typically, a needle with a stylet is inserted between the appropriate vertebrae, the stylet is removed and multiple vials are handled during the procedure. There is risk of breakage and leakage and consequent exposure of personnel to the samples collected. Also, when the needle or stylet is withdrawn during and after the procedure, there is risk of being stuck by either the needle or the stylet.

A number of systems have been devised to protect individuals from needle sticks while using syringes and angiocatheters. However, users of needles for other purposes, such as spinal taps, still have no protective devices suitable for their needs.

In U.S. Pat. No. 5,396,899, Strittmatter disclosed an apparatus to limit leakage when spinal fluid is collected.

In application Ser. No. 08/795,342 means were introduced to limit exposure to needle sticks, stylet sticks, and spinal fluid samples during the performance of a spinal tap.

The means introduced in application Ser. No. 08/795,342 for spinal taps are applicable for the collection of other body samples.

SUMMARY OF THE INVENTION

This application introduces means for the safe collection of spinal fluid and other body samples. The means introduced in application Ser. No. 08/795,342 are illustrated with additional examples in the figures. Furthermore, modifications to the means introduced in application Ser. No. 08/795,342 are introduced to demonstrate the utility of the invention in the collection of other body samples, such as, for example, blood samples and tissue biopsies.

The invention relates to the introduction of a system that decreases exposure to needle sticks and stylet sticks by capturing the needle and stylet within a cylinder as they are withdrawn from the body. The needle unit of the invention comprises a needle and a hub and, optionallly, may also comprise a stylet. The needle may be a solid needle, such as ones used in an angiocatheter, or a hollow needle, such as those used for spinal taps and tissue biopsies. A hollow needle may also contain a stylet, such as, for example, a conventional spinal tap stylet or a tissue biopsy stylet. Furthermore, as is the case in currently used means for tissue biopsies, the needle may be a cutting needle and the stylet a device to passively retain the cut tissue, or the stylet itself may be a cutting stylet.

It is an object of the present invention to provide means for limiting exposure to needle sticks from spinal tap needles during and after the performance of a spinal tap. It is another object of the present invention to provide means for limiting exposure to sticks from spinal tap stylets during and after the performance of a spinal tap.

It is a further object of the present invention to provide means for limiting exposure to spinal fluid samples during and after the performance of a spinal tap.

It is a further object of the invention to introduce means to limit exposure to needles used in obtaining body fluid and tissue samples.

It is yet another object of the invention to introduce means to limit user exposure to stylets used in body access procedures.

It is still another object of the invention to limit exposure to body fluid and tissue samples.

A body access system is disclosed which provides for the safe collection of samples and the safe administration of fluids. The system provides protection from inadvertent needle sticks in the collection of samples. The system can be utilized not only for the collection of blood but also for the collection of other body fluids and biopsies, such as, for example, spinal taps, liver biopsies, renal biopsies, pleural biopsies, pericardiocentesis, thoracocentesis, paracentesis, and dialysis. The system also provides protection from inadvertent exposure to the samples themselves, such as, for example, blood and spinal fluid.

This invention proposes the use of a protective cylinder into which a needle can be withdrawn. The needle hub is engaged and the needle is then withdrawn into the cylinder or the cylinder is pulled over the needle.

It is an object of this invention to introduce a body access system to protect a user from both inadvertent needle sticks and from inadvertent exposure to body samples.

It is another object of this invention to introduce a protective cylinder into which a needle can be withdrawn.

It is a further object of this invention to introduce needle hub engagement means that are engaged for the subsequent withdrawal of said needles into protective cylinders.

It is an object of this invention to introduce a protective sample collection device to prevent a user from being exposed to the sample collected.

It is another object of this invention to introduce a protective sample collection device to prevent a user from being exposed to the sample collected by gravity flow.

It is a further object of this invention to introduce a protective sample collection device to prevent a user from being exposed to the sample collected by a vacuum.

BRIEF DESCRIPTION OF THE DRAWINGS

FIG. 11a illustrates the use of a catheter with an assembly of the invention.

FIG. 11b illustrates a single port catheter.

FIG. 11c illustrates a multi-port catheter.

FIG. 12a is an exploded view of a container and an assembly of a transmission means and container holding means of the invention.

FIG. 12b illustrates the container of FIG. 12a being held in the assembly of FIG. 12a.

FIG. 13a illustrates the external connections of the assembly of FIG. 12b.

FIG. 13b illustrates a variation of the assembly illustrated in FIG. 13a.

FIG. 16a is a detailed cross-sectional view of another disposal unit of the invention.

FIG. 16b is a detailed cross-sectional view of another guide of the invention.

FIG. 16c is a detailed cross-sectional view of another needle unit of the invention.

DETAILED DESCRIPTION OF THE PREFERRED EMBODIMENT

The system is fully understood by referring to a description of the figures.

Figure 15:
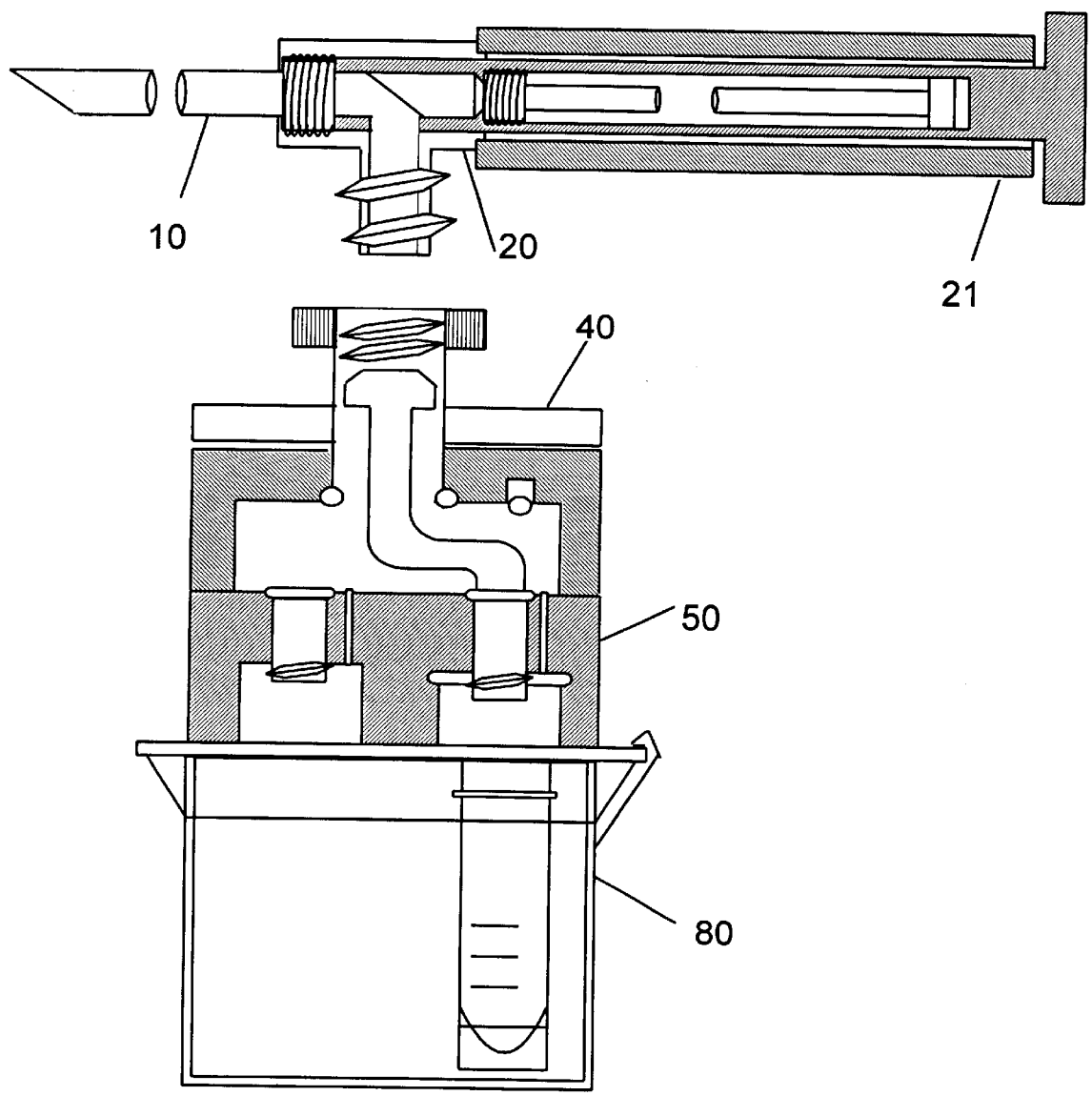
FIG. 15 is a cross-sectional view of a system of the invention.

FIG. 15 is a cross-sectional view of a system of the invention. The system illustrated in FIG. 15 is particularly suited for the performance of spinal taps.

Referring to FIG. 15, the system comprises needle unit 10, guide 20, disposal unit 21, transmission means 40, container holding means 50, and optional cover 80. One or more adapters, not shown, may also be included in the system to connect the guide to the transmission means. The hub of the needle unit is positioned within the guide. The guide and the hub are attached to the disposal unit. The guide is attachable either directly or indirectly to the transmission means. The transmission means and the container holding means function together as a unit. An optional cover is latched onto the container holding means and provides further protection in the event of breakage or leakage of one of the enclosed containers. Preferably, the parts of the system, especially the guide and the hub, are transparent to enable viewing the flow of fluid, such as the flow of spinal fluid during the spinal tap procedure.

When the system is used as described for a spinal tap, any spinal fluid collected will remain enclosed within the system and exposure to needle stick or spinal fluid will be minimized.

Prior to performing a spinal tap or other procedure, the user configures the system for his or her convenience. If the needle unit is not already positioned within the guide, the needle unit is inserted within the guide. If the disposal unit is attached to the guide and to the hub of the needle unit, the disposal unit is detached. If sample collection containers have not already been inserted into the container holding means or if the user desires different containers, the appropriate changes are made. Preferably, a cover is applied. And, the attachment of the guide to the transmission unit is configured as desired by the user. In the preferred embodiment, once the configuration is complete, the system is completely enclosed.

In the performance of a spinal tap, utilizing sterile technique, the user inserts the spinal needle into the subarachnoid space. The needle stylet is withdrawn and spinal fluid flows into the hub of the needle. The spinal fluid then flows from the hub, through a port in the guide and then either directly or through one or more adapters to the transmission means. In the embodiment depicted in FIG. 15, a flexible tube, not shown, conveys fluid from the guide to the adapter shown. The adapter is attached either directly or indirectly to the transmission means and spinal fluid flows through the adapter to the transmission means. Adapters are used for the convenience and preference of the individual user. However, the guide can be directly attached to the transmission means.

The transmission means and the container holding means function as a unit. These means are movable relative to each other. Movement of the transmission means relative to the container holding means or of the container holding means relative to the transmission means permits the sequential filling of sample containers held in the container holding means. Said movement may be circular, linear or any other displacement of the transmission means and the container holding means relative to each other which permits the sequential filling of sample containers held in the container holding means.

In the embodiment depicted in FIG. 15, the transmission means is rotatable relative to the container holding means. The container holding means holds one or more sample collection containers. Rotation of the transmission means of FIG. 15 enables the sequential filling of the sample collection containers held in the container holding means. When the desired amount of fluid has been collected in a given container, the transmission means is rotated and the next container is filled to the desired level. When the desired number of containers have been filled to their desired levels, the stylet is reinserted into the needle and the spinal needle is removed from the subarachnoid space.

Once the spinal tap procedure is completed, the disposal unit is attached to the guide and to the hub of the needle unit. The needle unit, including the stylet, is withdrawn into the disposal unit and the entire system is sent to the laboratory where the samples collected are removed for analysis and the system is disposed of under controlled conditions.

In FIGS. 16a, 16b and 16c the complementary relationship of needle unit 10, guide 20, and disposal unit 21 are illustrated.

The system uses a number of complementary engagement means. Complementary engagement means can be used, but are not required on transmitting and receiving ports. Transmitting and receiving ports are adapted to each other, using complementary engagement means or otherwise, such as by means of conventional seals, in order to limit leakage and to direct flow. Complementary engagement means are also used to maintain or establish an attachment of one part of the system to another part of the system. Specific complementary engagement means are illustrated and described for convenience of explanation. However, the complementary parts of any suitable fastener may be used as complementary engagement means in place of those illustrated and described. One example of complementary engagement means is an internal thread and an external thread. Another example of complementary engagement means is a snap comprising a hole and a projection, such as, for example, a plug or ball, which fits snugly into said hole. Thus, when an external thread is employed as the engagement means of the hub, an internal thread is employed as the engagement means of the disposal unit; or when an external thread is employed as the engagement means of the disposal unit, an internal thread is employed as the engagement means of the hub. Furthermore, instead of using a set of threads as the complementary engagement means of the hub and the disposal unit, another type of complementary engagement means, such as, for example, a snap can be used.

Referring to FIG. 16c, needle unit 10 comprises hollow needle 11, hub 12 and a needle stylet.

Preferably, needle 11 is permanently attached to hub 12 at the distal end of the hub. The hub comprises engagement means 15 at the distal end of the hub, engagement means 16 at the proximal end of said hub, chamber 18, and port 19. Port 19 communicates directly with chamber 18. When the stylet is removed from the lumen of the needle, spinal fluid flows through the lumen and an aperture at the distal end of the hub into chamber 18 of the hub. An aperture at the proximal end of the hub permits the slidable displacement of the stylus within the hub and the needle. The distal end of the stylus is wider than the aperture at the proximal end of the hub. The distal end 13 of the stylet is broader than the shaft 14 of the stylet. Preferably, the stylet is tapered from the distal end 13 to the shaft 14. Only the distal end of the stylet enters the subarachnoid space during a spinal tap procedure. During the performance of a spinal tap the stylet is withdrawn through the aperture at the proximal end of the hub. The cross-sectional dimensions of the aperture at the proximal end of the hub permit passage of the shaft of the stylet and prevent passage of the distal end of the stylet. Upon optimal withdrawal of the stylet, the distal end of the stylet remains within the hub but does not occlude the flow of spinal fluid through any port in the hub. That is, optimal withdrawal of the stylet permits unobstructed flow through any port in the hub. The shaft of the stylet fits snugly in the aperture at the proximal end of the hub to limit any leakage of spinal fluid. Since only the shaft is small enough to pass through the aperture at the proximal end of the needle hub, upon maximum withdrawal of the stylet from the needle, the end of the stylet which had entered the subarachnoid space remains within the needle hub.

Guide 20 comprises engagement means 25 at the distal end of the guide, engagement means 17 at the proximal end of the guide, chamber 28, and port 29. Engagement means 25 is complementary to engagement means 15. Hub 12 is securely positioned within guide 20 by the engagement of engagement means 15 and engagement means 25. In the illustration of FIGS. 16a, 16b and 16c engagement means 15 and engagement means 25 are threads. However, any suitable complementary means can be substituted for these threads. Port 29 of guide 20 is aligned with port 19 of hub 12 so that spinal fluid in chamber 18 of the hub flows through port 19 and then through port 29.

Figure 2A:
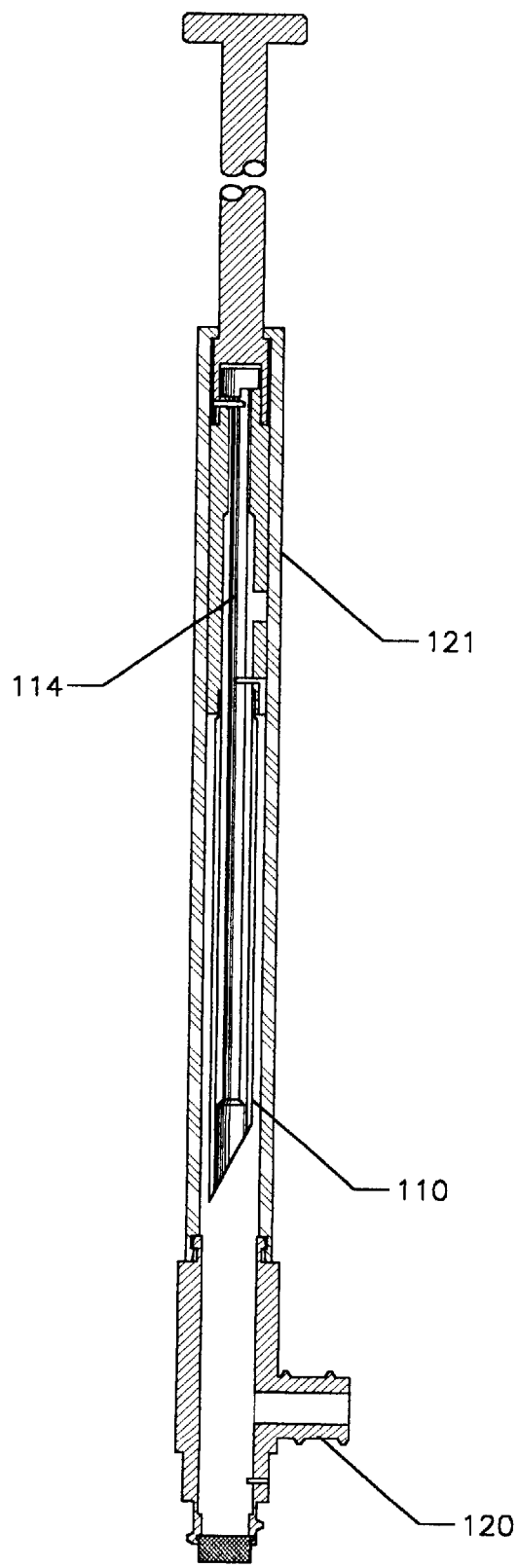
FIG. 2 is a cross-sectional view of an assembly of the disposal unit, stylet, needle unit and guide illustrated in FIG. 1.
Figure 2B:
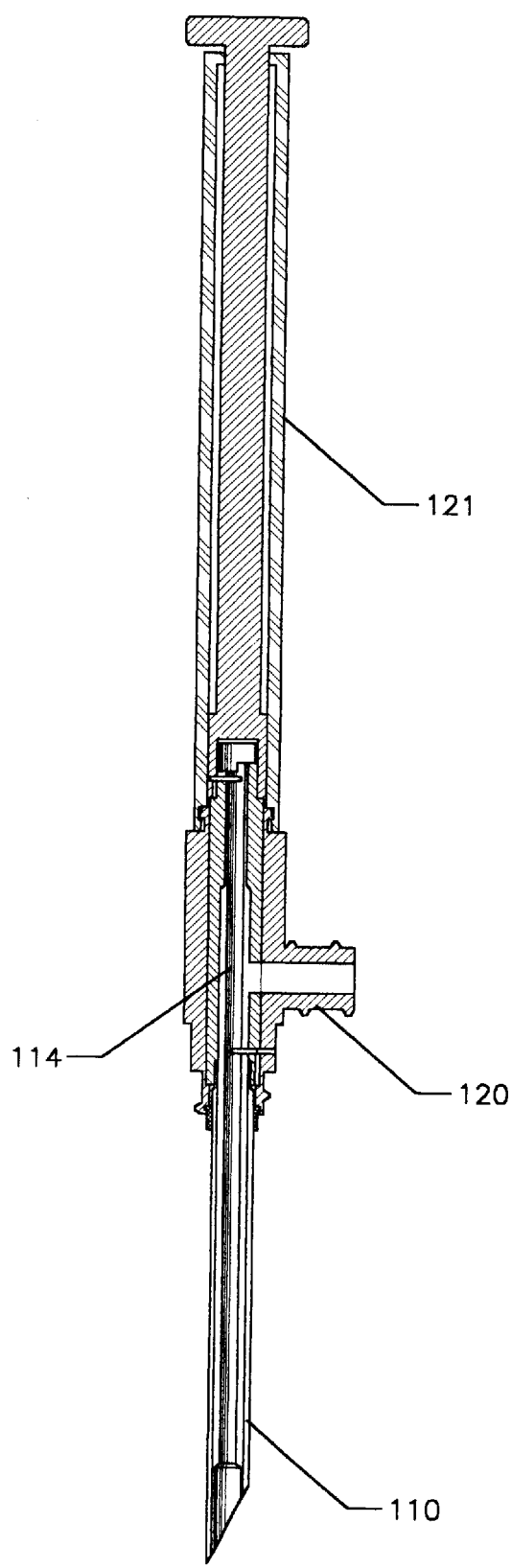

Disposal unit 21 comprises rigid cylinder 22 and plunger 23. Rigid cylinder 22 comprises engagement means 27 at the distal end of the rigid cylinder and plunger 23 comprises engagement means 26 at the distal end of the plunger. Engagement means 27 is complementary to engagement means 17. Rigid cylinder 22 securely attaches to guide 20 by the engagement of engagement means 17 and engagement means 27. Engagement means 17 and engagement means 27 are any suitable complementary engagement means such as, for example, threads. At the end of the spinal tap procedure, the user engages engagement means 27 and engagement means 17 to securely hold and stabilize guide 20. Then the user engages engagement means 26 and engagement means 16. Engagement means 26 is complementary to engagement means 16. Preferably, the engagement of engagement means 27 and engagement means 17 prevents the rotation of guide 20. Hub 12 is removed from within guide 20 by the engagement of engagement means 16 and engagement means 26 and the simultaneous disengagement of engagement means 15 and engagement means 25. In the illustrations of FIGS. 2a, 2b, and 2c engagement means 16 and engagement means 26 are threads. However, any suitable complementary means can be substituted for these threads. In the embodiment illustrated, the threading of complementary engagement means 15 and 25 are the reverse of the threading of complementary engagement means 16 and 26 so that a turning of plunger 23 to engage engagement means 16 and 26 simultaneously disengages engagement means 15 and 25. Once engagement means 15 are disengaged from engagement means 25, the user can turn or pull plunger 23 to withdraw the needle unit into the disposal unit.

In FIGS. 16a, 16b and 16c plunger 23 is internally threaded to engage the externally threaded distal end of hub 12. If the entire length of the internally threaded plunger 23 is threaded and the external threads of the distal end of the hub are of suitable diameter, for example, greater than the diameter of the remainder of said hub, when the hub is engaged by the plunger, a turning of the plunger withdraws the needle unit into the disposal unit.

If only a segment of plunger 23 is internally threaded to engage the externally threaded distal end of hub 12, when the hub is engaged by the plunger, a pulling of the plunger withdraws the needle unit into the disposal unit.

Figure 17A:
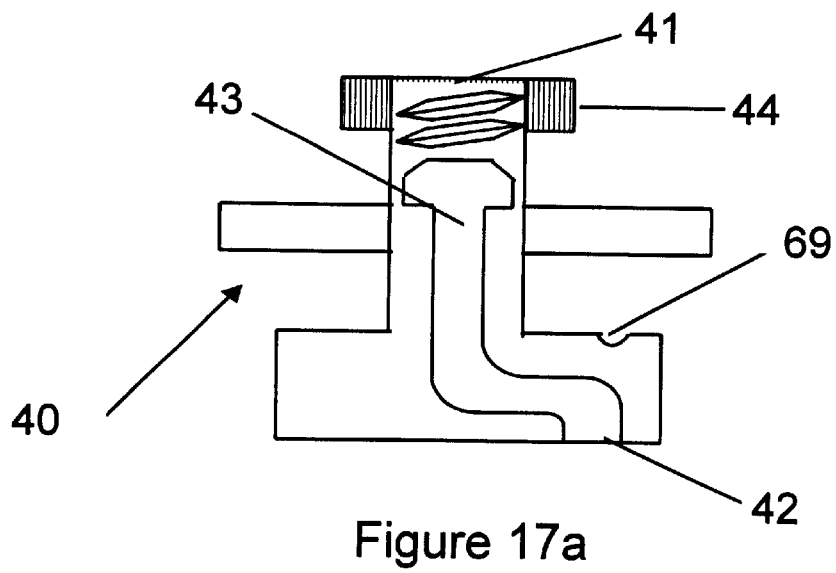
FIG. 17a is an exploded cross-sectional view of the transmission means of the invention.
Figure 17B:
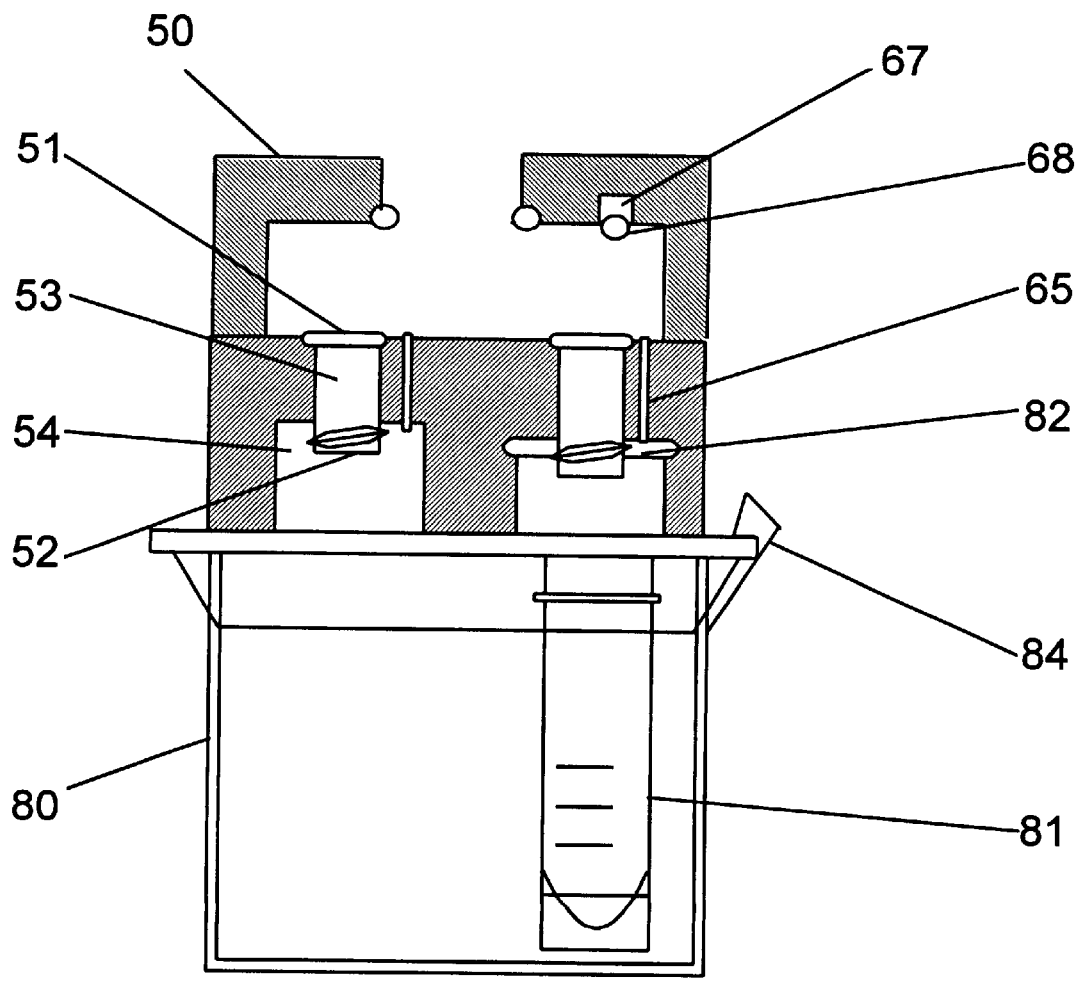
FIG. 17b is an exploded cross-sectional view of the container holding means of the invention.

FIGS. 17a and 17b depict detailed cross sections of transmission means 40 and container holding means 50. Cover 80 is reversibly attached to the container holding means by latch 84.

The transmission means comprises a channel to transmit fluid from a needle unit to a container holding means. Either a needle unit or as guide is adapted to engage the transmission means either directly or by means of one or more adapters. The transmission unit is also adapted to engage a sample container, either directly or by means of one or more adapters. Thus, the transmission unit is adapted to receive fluid from the needle unit and to transmit fluid from the needle unit to the container. For example, as illustrated in FIGS. 3a and 3b, transmission means 40 comprises external port 41, channel 43 and internal port 42. External port 41 is adapted to engage port 29 of guide 20, or the port of an adapter. That is, external port 41 and port 29 are complementary engagement means. Spinal fluid received either directly or indirectly from port 29 at external port 41 then flows through channel 43 to internal port 42.

Container holding means 50 comprises at least one adapter 53, and at least one container holding recess 54. Adapter 53 comprises an external port 51 and an internal port 52. Sample container 81 comprises an optional cap 82. Each sample container comprises a port that is adapted to engage internal port 52 of adapter 53. In the embodiment illustrated, cap 82 comprises the port adapted to engage internal port 52 of adapter 53. In operation, a container 81 is positioned in one or more container holding recesses 54. Adapter 53 is adapted at external port 51 to receive spinal fluid from internal port 42 of transmission means 40 and adapted at internal port 52 to transmit said spinal fluid to the port of a sample container or a sample container cap. That is, external port 51 and internal port 42 are complementary engagement means and internal port 52 and the port of the sample container are complementary engagement means.

The transmission means and the container holding means are movable relative to each other. In the embodiment illustrated, said movement is a circular rotation. The transmission means preferably comprises an internally threaded engagement means 44 adapted to engage the external threads of port 29 or the external threads of a port of an adapter. Engagement means 44 is rotatably attached to the transmission means. When engagement means 44 engages the external threads of port 29 or the external threads of a port of an adapter, port 41 is securely but rotatably engaged to port 29 or an externally threaded port of an adapter and port 41 is freely rotatable relative to port 29. Preferably, engagement means 29 and engagement means 41 are seals, such as, for example, O-rings, which are sealably pressed together when engagement means 44 engages the external threads of port 29.

In the embodiment illustrated in FIGS. 17a and 17b, spinal fluid flows from external port 41 through channel 43 to internal port 42. Flow continues through port 42, into port 51, through adapter 53 to port 52. From port 52 flow then goes through a port in cap 82 into container 81. Once the desired quantity of fluid is collected in a sample container, the transmission means is rotated until port 52 engages a port in another cap 82. Preferably, the interface between the transmission means and the top of the containers is a seal, such as an O-ring, which prevents leakage from filled containers. Thus, once a container is filled to the desired level, the rotation of the transmission means to enable the filling of the next container in sequence, also seals the tops of containers which have already been filled.

Preferably, in order to prevent leakage, an O-ring or other seal is placed between the transmission means and the container holding means, between ports 29 and 41, between ports 42 and 51, between port 52 a port in cap 82, and in any other part of the system where leakage might occur. The seal between the transmission means and the container holding means is utilized to prevent leakage from sample containers. Also, it is preferred to include an index means in the system which will stop rotation of the transmission means when port 52 engages and is aligned with a port in another cap 82. Any suitable index means can be used. For example, the index means illustrated comprises ball 68, spring 67, and hemispherical indent 69. During rotation of transmission means 40, whenever ball 68 engages a hemispherical indent 69, the tension of spring 67 forces ball 68 into a hemispherical indent 69 and stops said rotation. A slight force is applied by the operator to overcome the resistance of the spring so that the transmission means can be rotated to the next desired position. It is preferred that a brake be provided after the filling of the last sample container. Said brake functions in the same manner as the index means and can utilize the same ball and spring with the replacement of the hemispherical indent with a deeper indent. When the ball falls into said deeper indent, further rotation of the transmission means is prevented. There is one hemispherical indent 69 or a brake for each recess 54. It is also preferred that air vents 65 be provided where needed to enable release of air through caps 82 during the filling of containers 81.

Figure 1:
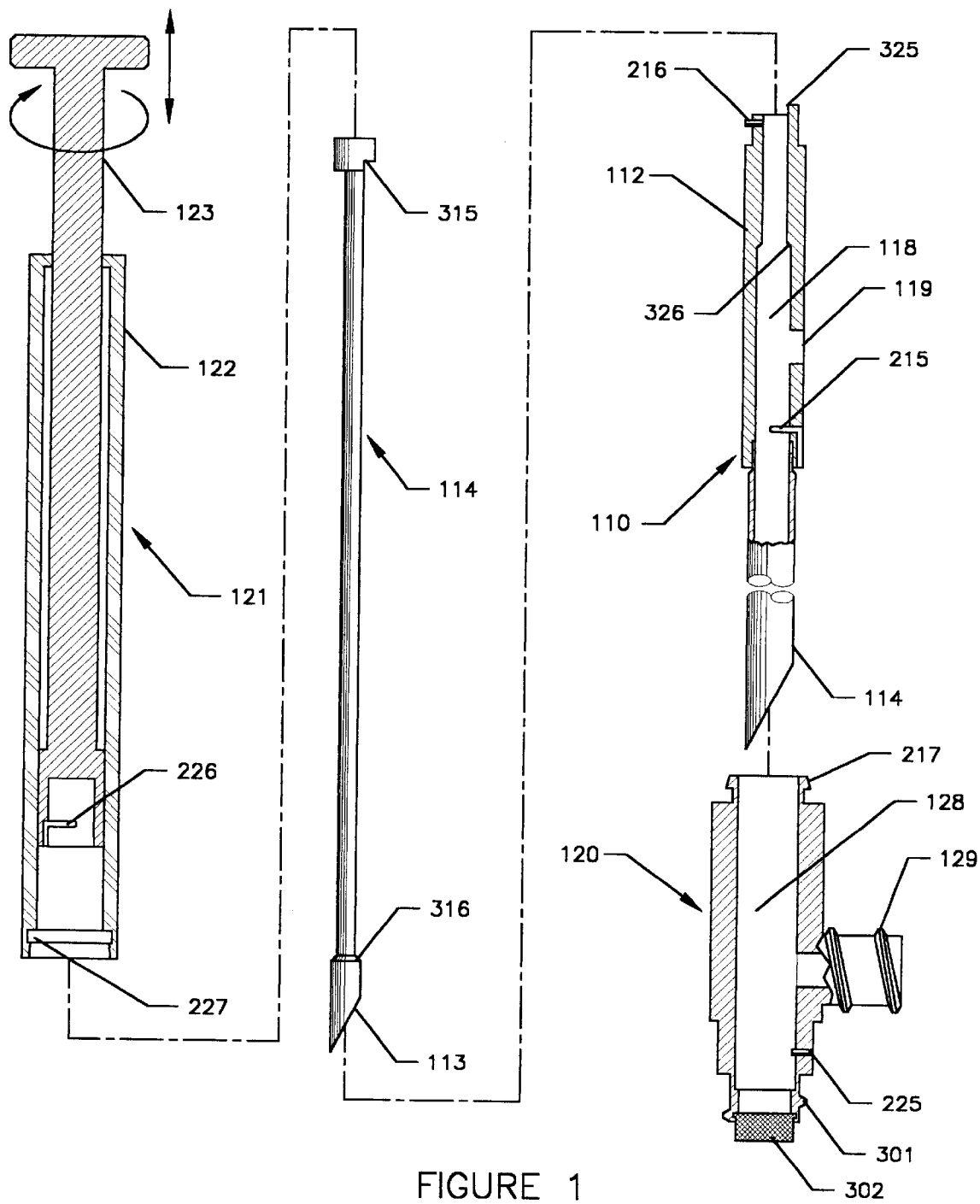
FIG. 1 is a cross-sectional view of a disposal unit, a stylet, a needle unit and a guide.

In FIG. 1 the complementary relationship of needle unit 110, guide 120, and disposal unit 121 are illustrated. Needle unit 110 comprises hollow needle 111, hub 112 and needle stylet 114.

Preferably, needle 111 is permanently attached to hub 112 at the distal end of the hub. The hub comprises engagement means 215 at the distal end of the hub, engagement means 216 at the proximal end of said hub, chamber 118, and port 119. Port 119 communicates directly with chamber 118. When the stylet is removed from the lumen of the needle, fluid flows through the lumen and an aperture at the distal end of the hub into chamber 118 of the hub. An aperture at the proximal end of the hub permits the slidable displacement of the stylet within the hub and the needle. Distal end 113 of stylet 114 is wider than the aperture at the proximal end of the hub. Distal end 113 of stylet 114 is broader than the shaft of stylet 11. Preferably, the stylet is tapered from the distal end to the shaft. Only the distal end of the stylet enters the subarachnoid space during a spinal tap procedure. During the performance of a spinal tap the stylet is withdrawn through the aperture at the proximal end of the hub. The cross-sectional dimensions of the aperture at the proximal end of the hub permit passage of the shaft of the stylet and prevent passage of the distal end of the stylet. Proximal end 326 of chamber 118 is shaped to prevent complete removal of the stylet from the hub. Upon optimal withdrawal of the stylet, the distal end of the stylet remains within the hub but does not occlude the flow of spinal fluid through any port in the hub. That is, optimal withdrawal of the stylet permits unobstructed flow through any port in the hub. The shaft of the stylet fits snugly in the aperture at the proximal end of the hub to limit any leakage of spinal fluid. Since only the shaft is small enough to pass through the aperture at the proximal end of the needle hub, upon maximum withdrawal of the stylet from the needle, the end of the stylet which had entered the subarachnoid space remains within the needle hub. Preferably, upon maximum withdrawal of the stylet, the stylet is firmly held in the maximal withdrawal position such that the stylet will remain in the maximally withdrawn position, and will not fall, even if positioned vertically with the stylet tip pointed downward. Thus, for example, when proximal end 326 of chamber 118 engages proximal end 316 of distal end 113 of stylet 114, stylet 114 is firmly held in place by friction regardless of the position of hub 112.

Guide 120 comprises engagement means 225 at the distal end of the guide, engagement means 217 at the proximal end of the guide, chamber 128, and port 129. Engagement means 225 is complementary to engagement means 215. Hub 112 is securely positioned within guide 120 by the engagement of engagement means 215 and engagement means 225. In the illustration of FIG. 1 engagement means 215 is a slot and engagement means 225 is a pin of a bayonet mount. However, any suitable complementary means can be substituted for this bayonet mount. When assembled, as in FIG. 2, port 129 of guide 120 is aligned with port 119 of hub 112 so that spinal fluid in chamber 118 of the hub flows through port 119 and then through port 129.

Disposal unit 121 comprises rigid cylinder 122 and plunger 123. Rigid cylinder 122 comprises engagement means 227 at the distal end of the rigid cylinder and plunger 123 comprises engagement means 226 at the distal end of the plunger. Engagement means 227 is complementary to engagement means 217. Rigid cylinder 122 securely attaches to guide 120 by the engagement of engagement means 217 and engagement means 227. Engagement means 217 and engagement means 227 are any suitable complementary engagement means such as, for example, the threads of a leur lock. At the end of a spinal tap or other procedure, the user engages engagement means 227 and engagement means 217 to securely hold and stabilize guide 120. Then the user engages engagement means 226 and engagement means 216. Engagement means 226 is complementary to engagement means 216. Preferably, the engagement of engagement means 227 and engagement means 217 prevents the rotation of guide 120. Hub 112 is removed from within guide 120 by the engagement of engagement means 216 and engagement means 226 and the simultaneous disengagement of engagement means 215 and engagement means 225. In the illustrations of FIG. 1, engagement means 216 is a pin and engagement means 226 is a slot of a bayonet mount. However, any suitable complementary means can be substituted for this bayonet mount. In the embodiment illustrated in FIG. 1, the engagement of complementary engagement means 215 and 225 are the reverse of the engaging of complementary engagement means 216 and 226 so that a turning of plunger 123 to engage engagement means 216 and 226 simultaneously disengages engagement means 215 and 225. Once engagement means 215 are disengaged from engagement means 225, the user pulls plunger 123 to withdraw the needle unit into the disposal unit.

Notch 315 at the proximal end of stylet 114 and ridge 325 at the proximal end of hub 112 are optional complementary orientation means used to properly aligned the stylet within the needle. Optional adapter means can also be provided such as, for example, the leur lock thread 301 at the distal end of guide 120. Another option is the provision of an adhesive or silicon sealant to provide a penetrable seal means to prevent fluid flow through the guide port. Similar seals and adapters can be used in other components of the invention such as, for example, the ports of the needle hub.

FIG. 2 is a cross-sectional view of an assembly of the disposal unit, stylet, needle unit and guide illustrated in FIG. 1. In FIG. 2b the needle is fully extended and the disposal unit attached as would be the case just after the completion of a procedure such as, for example, a spinal tap. In FIG. 2b, the needle and hub have been withdrawn into the disposal unit. Note that the cavity at the distal end of plunger 123 accommodates the proximal end of stylet 114.

Figure 3:
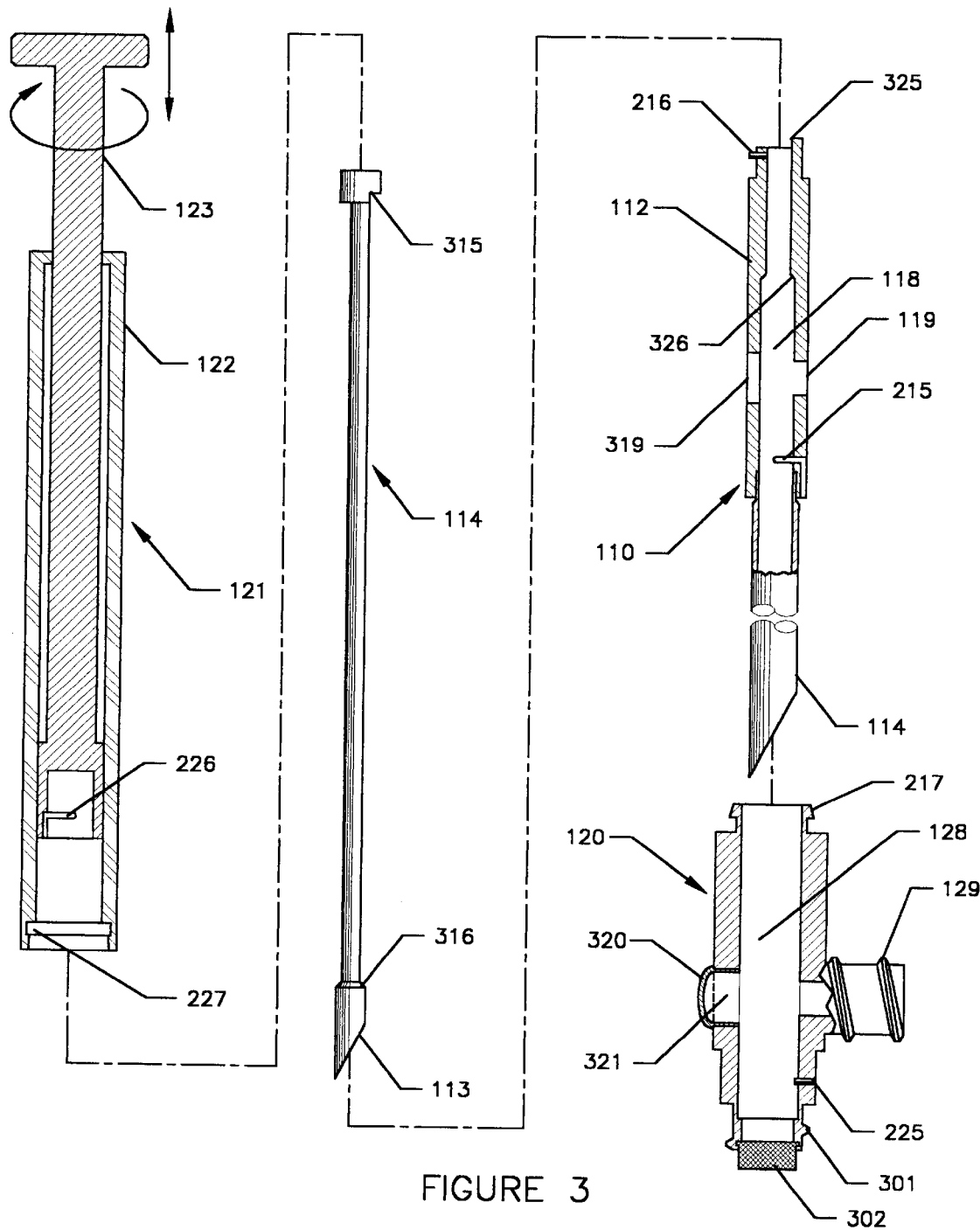
FIG. 3 is a cross-sectional view of another embodiment of a disposal unit, stylet, needle unit and guide of the invention.
Figure 4:
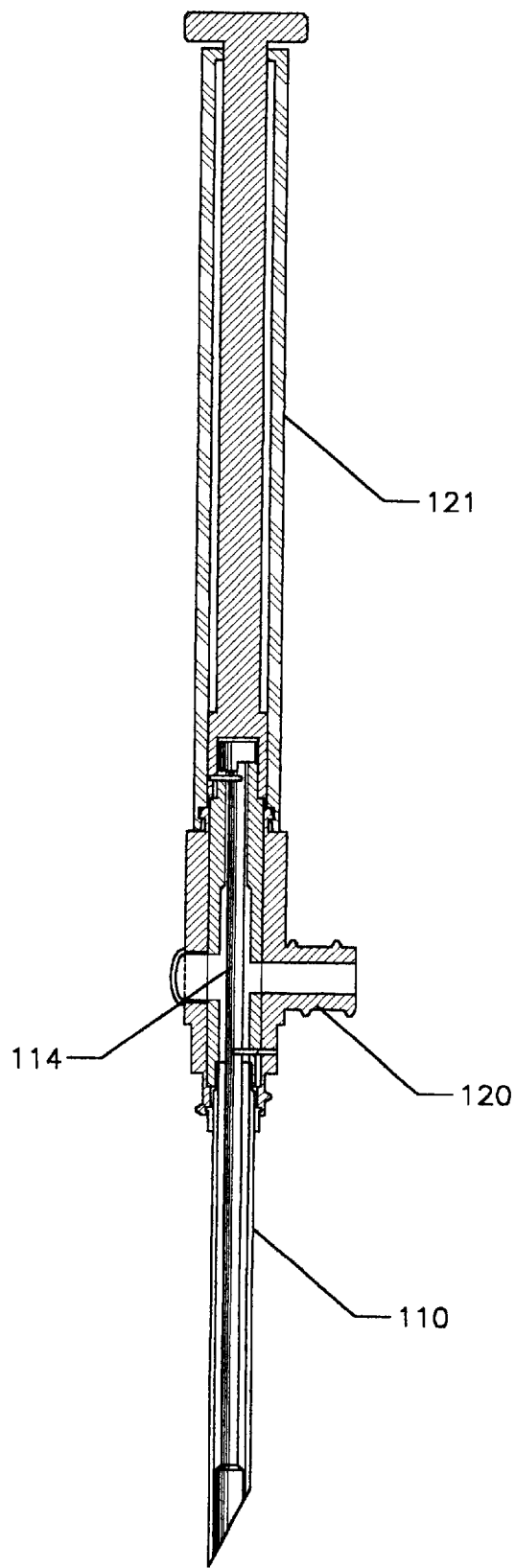
FIG. 4 is a cross sectional view of an assembly of the disposal unit, stylet, needle unit and guide illustrated in FIG. 3.
Figure 5:
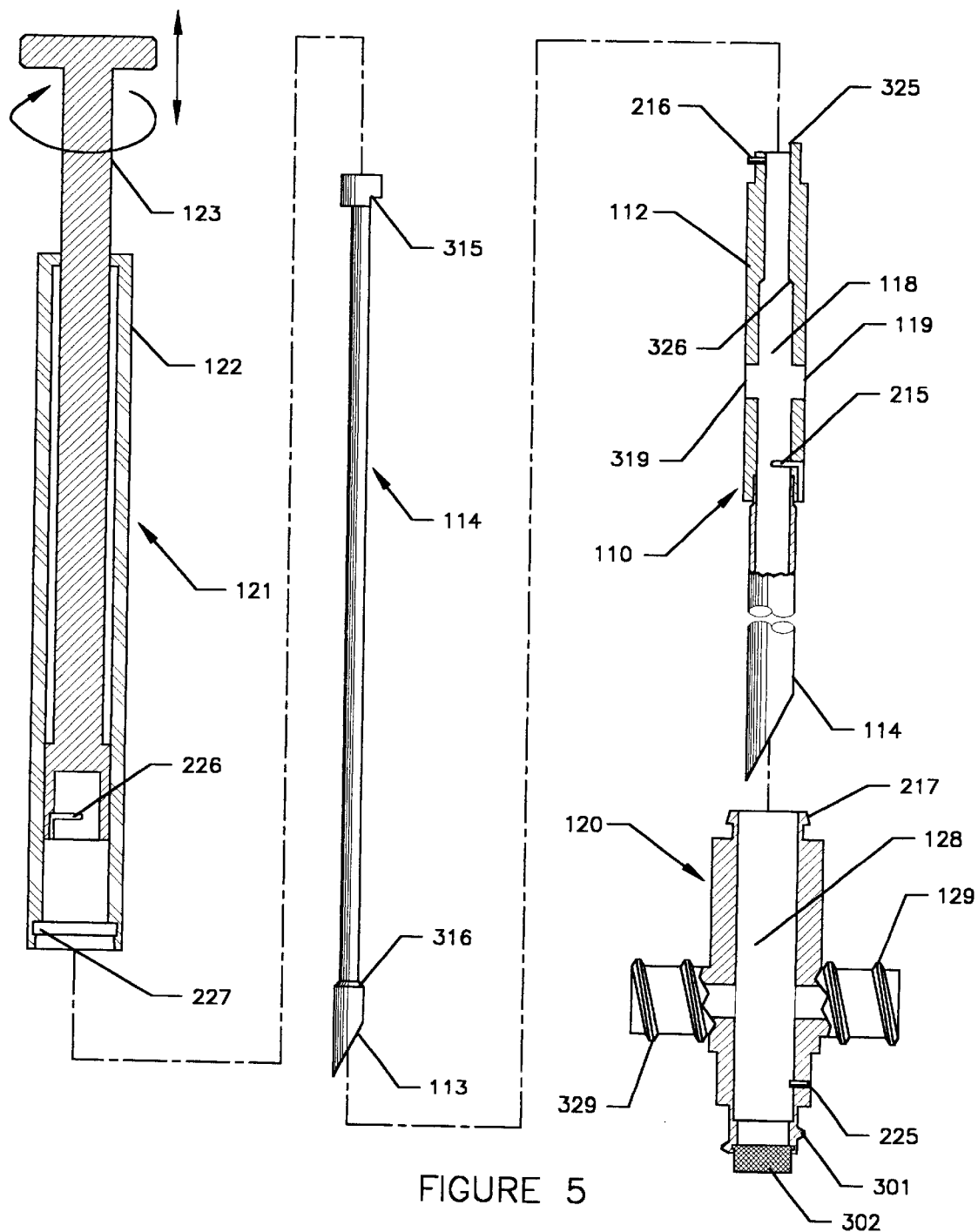
FIG. 5 is a cross-sectional view of another embodiment of a disposal unit, stylet, needle unit and guide of the invention.
Figure 6:
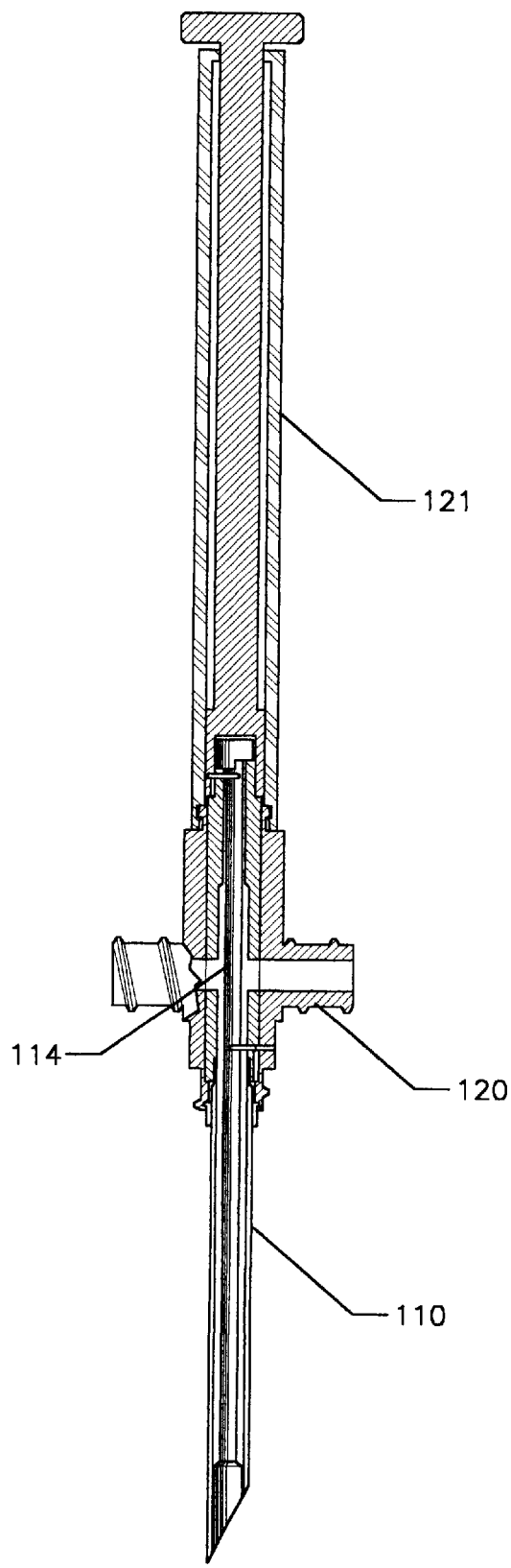
FIG. 6 is a cross sectional view of an assembly of the disposal unit, stylet, needle unit and guide illustrated in FIG. 5.

FIGS. 3 and 5 illustrate optional features that can be added to the components illustrated in FIG. 1. In FIG. 3, guide chamber 321 and window 320 are provided to allow viewing of fluid flow into the hub as the needle is withdrawn. In FIG. 5, port 329 is an additional port in guide 120. Port 319, illustrated in FIGS. 3 and 5, communicates with optional guide chamber 321 when the hub is properly aligned within the guide as illustrated in FIG. 4 and communicates with optional port 329 when the hub is properly aligned within the guide as illustrated in FIG. 6.

Figure 7:
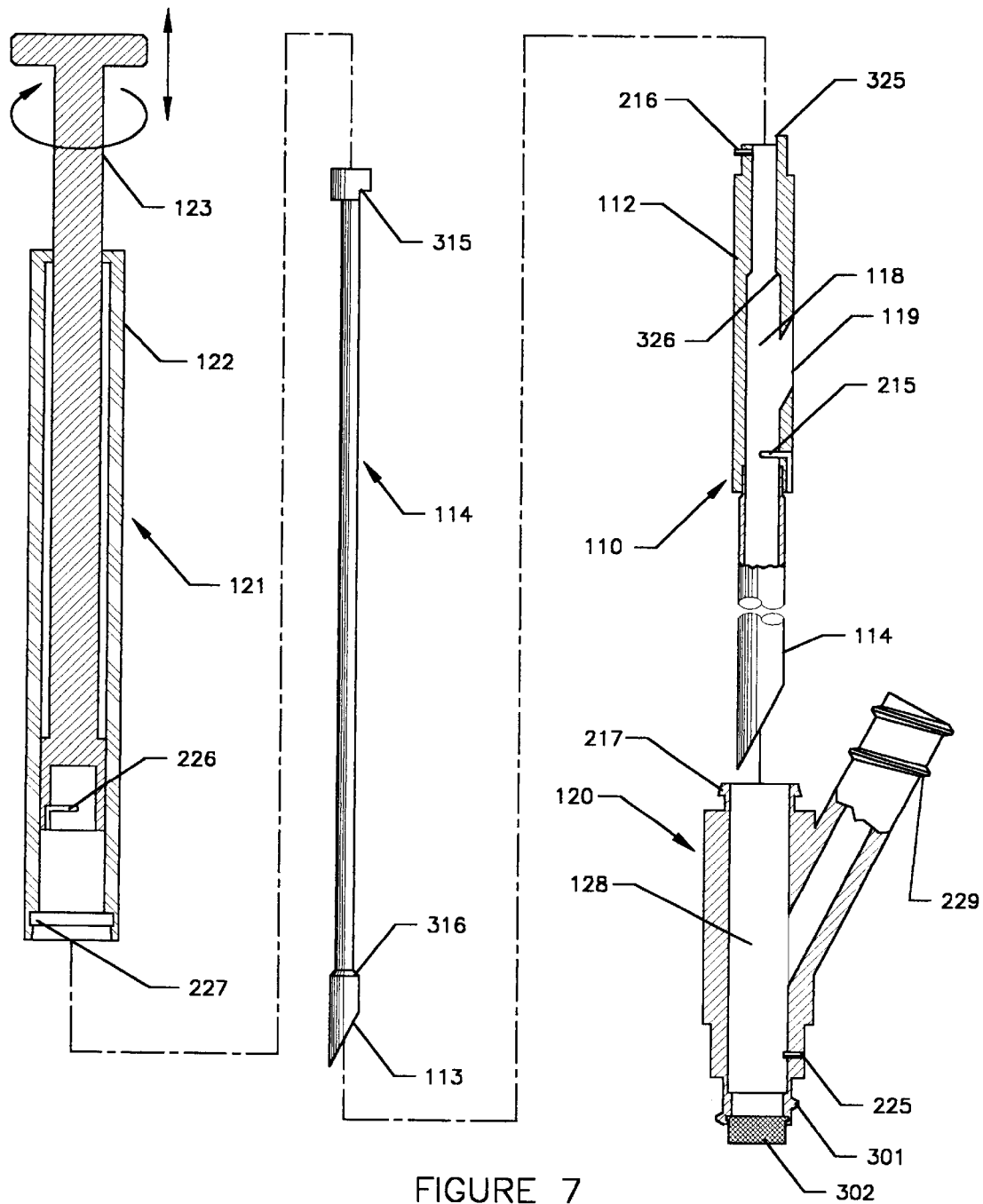
FIG. 7 is a cross-sectional view of another embodiment of a disposal unit, stylet, needle unit and guide of the invention.
Figure 8:
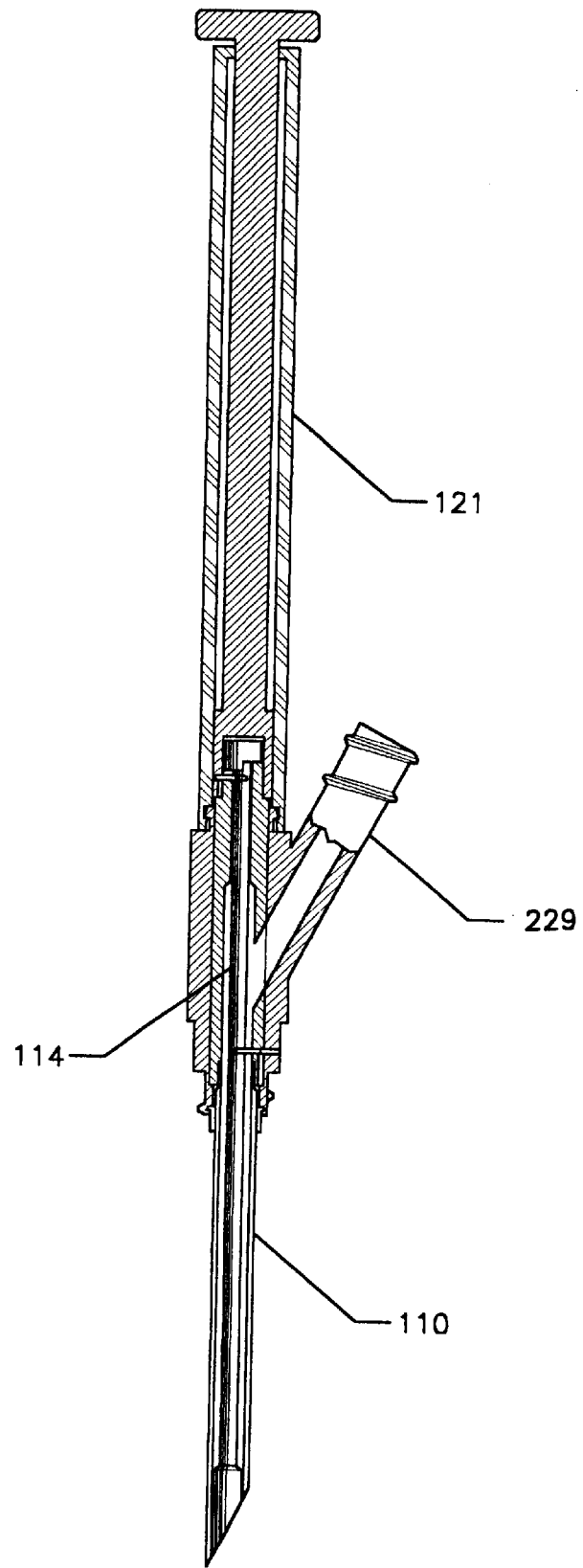
FIG. 8 is a cross sectional view of an assembly of the disposal unit, stylet, needle unit and guide illustrated in FIG. 7.

FIG. 7 illustrates that the shape of port 119 is variable and is dependent on the type of port to which it will be aligned, such as port 229 of the guide. The angle of the ports of the guide and hub depend on the application for which they will be used. FIG. 8 illustrates the alignment of ports 119 and 229 of FIG. 7 when the hub is properly aligned within the guide. In conjunction with a spinal tap or epidural needle, when the stylet is optimally withdrawn, a port angled like port 229 in FIGS. 7 and 8 may serve to insert an epidural catheter.

Figure 9:
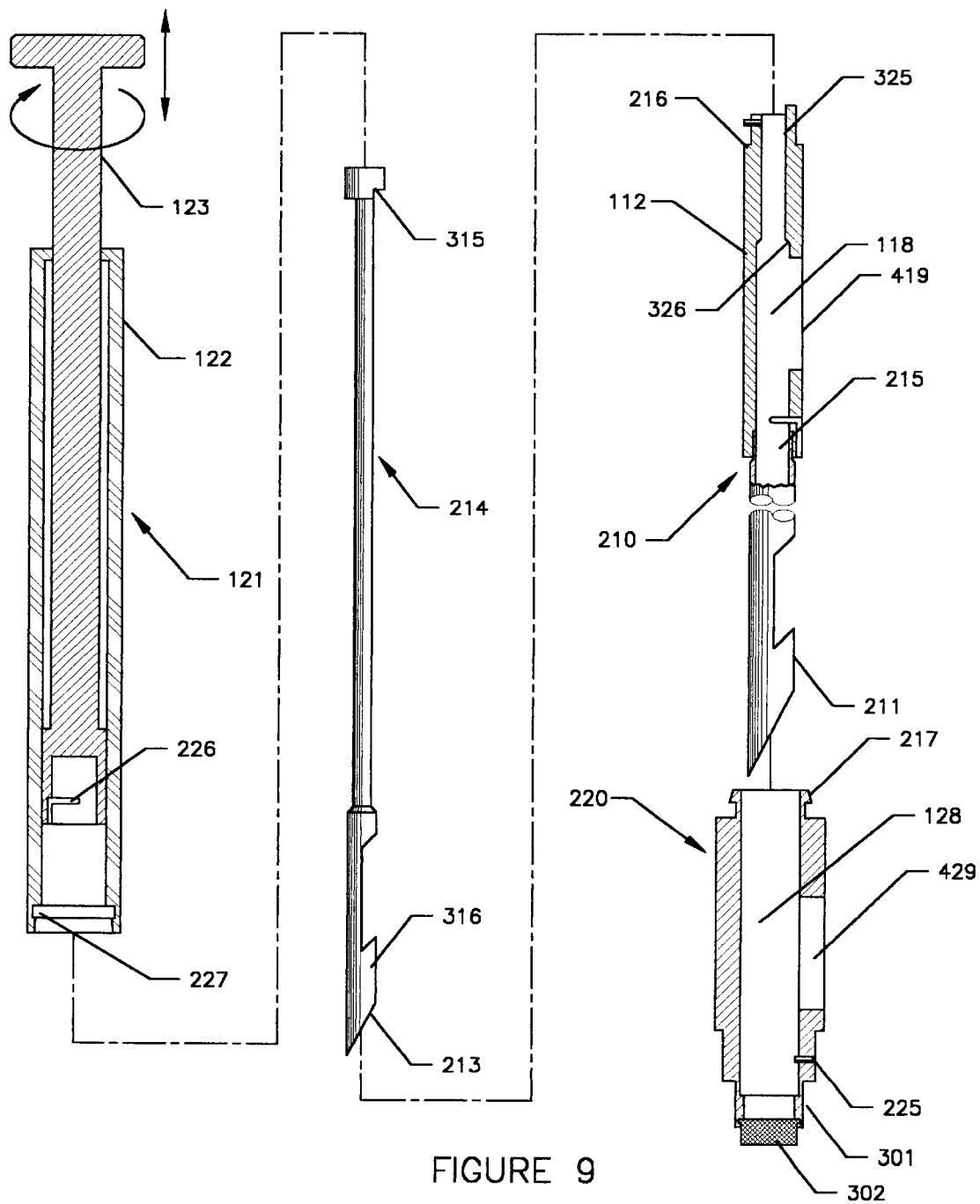
FIG. 9 is a cross-sectional view of another embodiment of a disposal unit, stylet, needle unit and guide of the invention.

FIGS. 9 and 10 illustrate the application of the invention to biopsy needles and stylets.

Figure 10A:
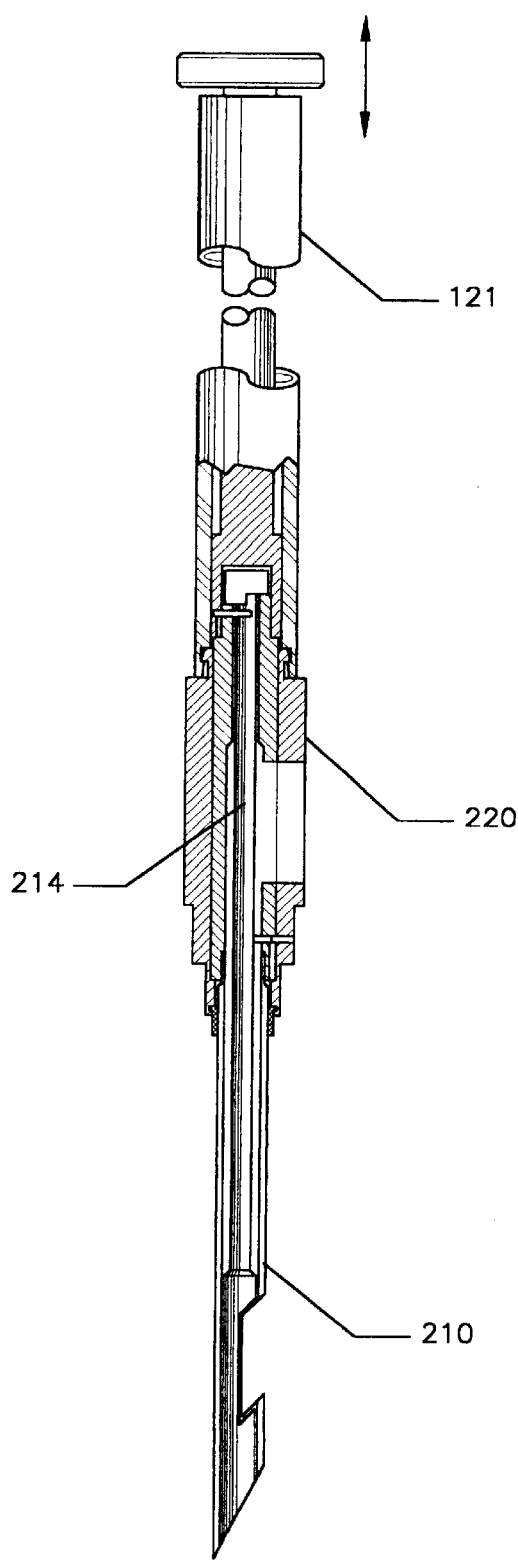
FIG. 10 is a cross sectional view of an assembly of the disposal unit, stylet, needle unit and guide illustrated in FIG. 9.
Figure 10B:
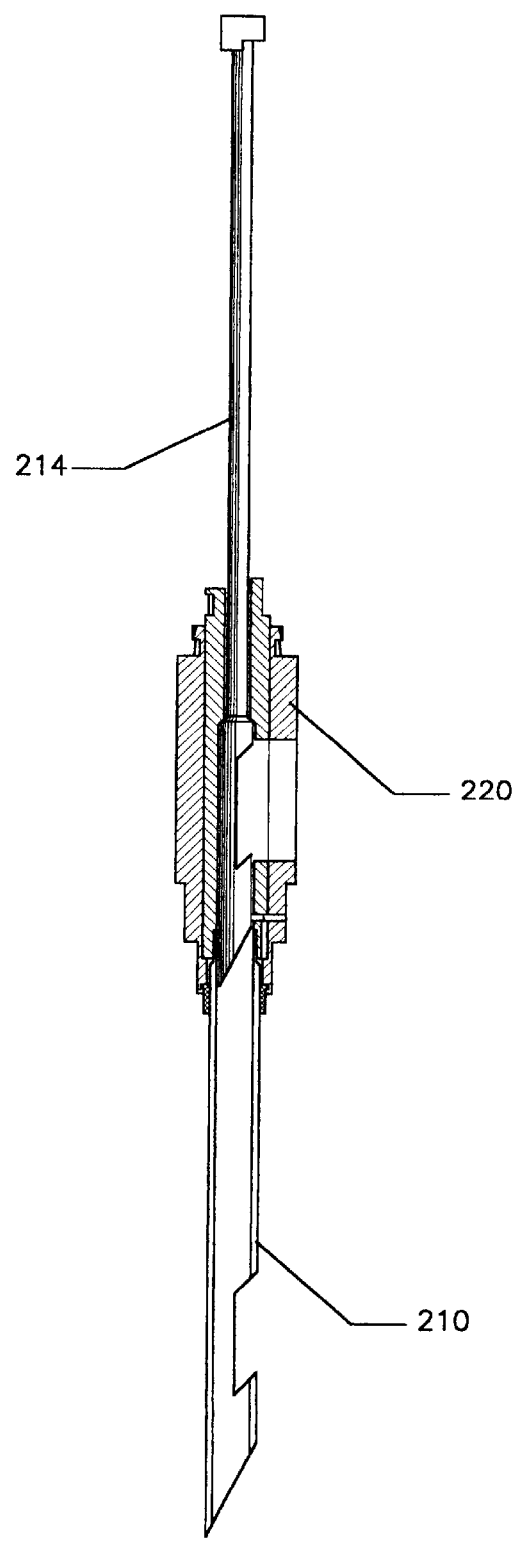

In FIG. 9, cutting stylet 214 is illustrated. Distal end 213 of cutting stylet 214 comprises a recess. Also illustrated in FIG. 9 is needle unit 210, which comprises needle 211. Needle 211 comprises a recess. Also illustrated are ports 419 and 429. It is noted that the size and shapes of these ports is dependent on the purpose for which they are used. FIG. 10a illustrates the alignment of the components of FIG. 9 when the cutting stylet is fully inserted into the needle and FIG. 10b illustrates an alignment of the components when the stylet withdrawn. It is noted that various combinations of biopsy stylets and needles can be used in this invention. For example, a cutting needle with a cutting recess can be used in conjunction with a stylet without a recess. In another example, a cutting stylet with a recess can be used with a needle without a recess. The exact biopsy stylet and needle used will depend on the method used for obtaining a biopsy.

In one conventional procedure for the performance of biopsies, a cutting stylet is inserted through a needle or rigid catheter into the body tissue to be biopsied. The distal end of the cutting stylet extends beyond the distal end of the needle or catheter into the tissues to be biopsied and is then withdrawn back into the catheter or needle. Upon withdrawal of the cutting stylet, the stylet cuts the tissue to be biopsied and retains a piece of the cut tissue in a recess in the cutting stylet.

An alternative procedure is to insert a stylet with a recess into the tissue to be biopsied. A piece of the tissue to be biopsied settles into the recess. A cutting needle is then inserted over the stylet and cuts the piece of tissue that settled into the recess. The stylet remains within the needle and then the stylet and needle are withdrawn together along with the tissue trapped inside the recess. In this method, the stylet and cutting needle are inserted together; the distal end of the stylet is then extended beyond the distal end of the cutting needle, and then the cutting end of the cutting needle is push towards the distal end of the stylet to cut the tissue trapped in the recess. In the alternative, the stylet is first inserted and then the cutting needle, using the stylet as a guide, is inserted over the stylet to cut the tissue trapped in the recess.

In another alternative method, a needle with a stylet is inserted into the tissue to be biopsied, the stylet is at least partially withdrawn and the needle is rotated and/or pushed further into the tissue to obtain a core of tissue. Subsequently, after the needle is withdrawn, the stylet is used to push the tissue obtained back out of the needle.

In a further alternative method, a needle with a stylet is inserted into the tissue to be biopsied, the stylet is withdrawn to uncover a cutting recess in the needle and the needle is withdrawn. As the needle is withdrawn, tissue is cut and retained in the needle cutting recess.

Accordingly, in some instances, the biopsy stylet is longer than the needle so that it can extend beyond the needle at some point in time during the procedure. It follows that, when the distal end of the stylet is withdrawn to rest completely within the needle, the length of the stylet that extends beyond the proximal end of the needle hub is dependent on the length of the stylet. Furthermore, since the cavity at the distal end of the plunger accommodates the proximal end of the stylet, the depth of the cavity varies with the length of the stylet.

FIG. 11 illustrates the use of catheters with the invention. Ports 129 and 301 comprise engagment means to which complementary egagement means can be affixed. As illustrated in FIGS. 11a, 11b and 11c, catheters 411 and 412 comprise engagement means, such as leur locks, 311 and 312 that can engage an engagement means on port 301. Each engagement means 311 and 312 comprises seal 413. Seal 413 is a seal, such as a capless valve, which is closed when not engaged by complementary egagement means and open when engaged by complementary engagement means. When used in conjunction with a spinal tap needle or epidural needle, catheters such as those illustrated in FIGS. 11a, 11b and 11c may serve as introducers for epidural catheters.

FIGS. 12a, 12b, 13a, 13b and 14 illustrate the collection valve module introduced in this invention. Each collection valve module comprises a transmission means and a valve switch. Fluid received by a transmission means is transmitted to a collecting tube when a valve switch is open.

Figures 12A, 12B:
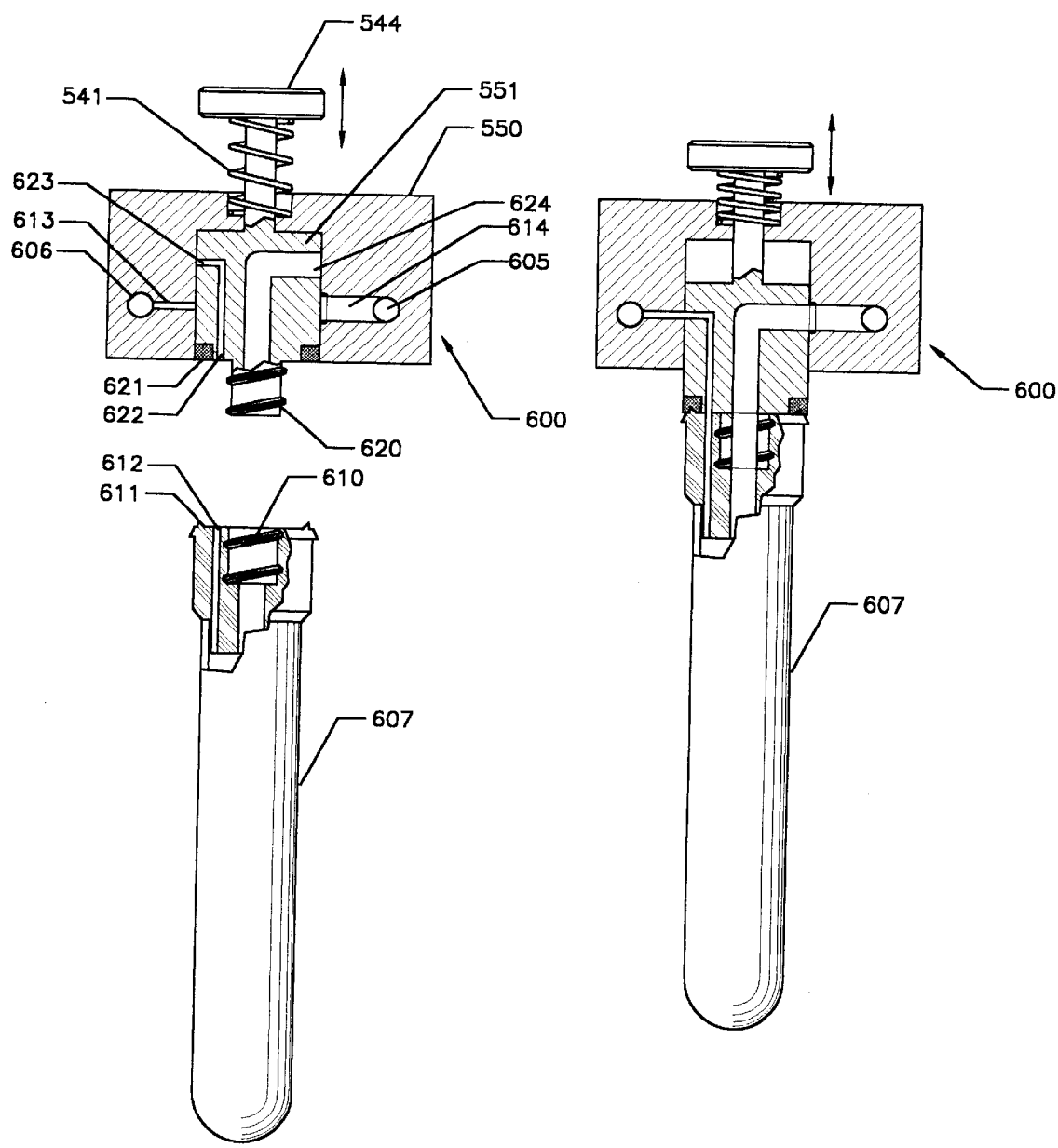
Figures 13A, 13B:
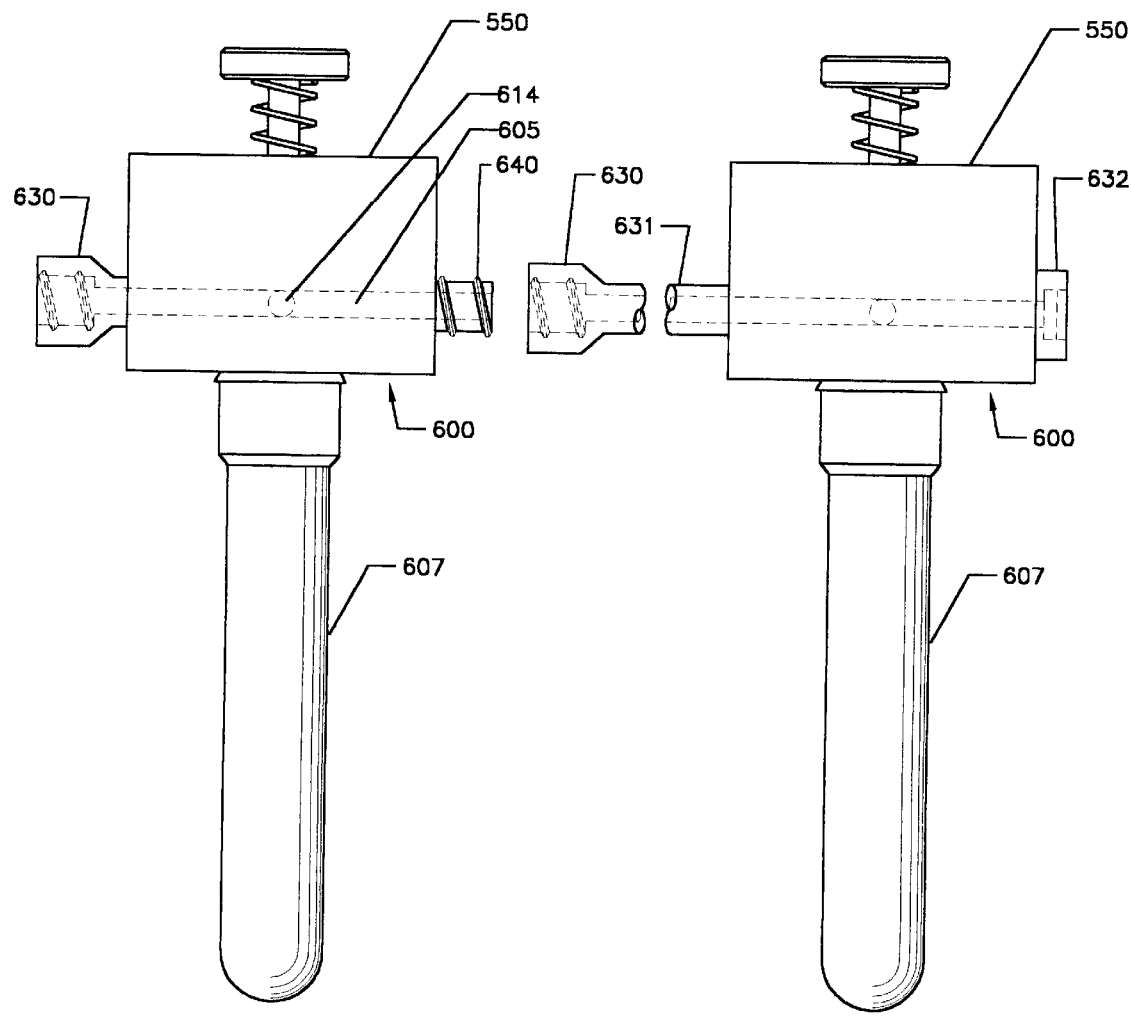

FIGS. 12a and 12b depict detailed cross sections of collection valve module 600. Each module comprises transmission means 550 and valve switch 551.

Fluid received by transmission means 550 is transmitted to a collecting tube when valve switch 551 is open.

Transmission means 550 comprises channel 605 to transmit fluid from a needle unit to a container through internal port 614 and valve switch 551 when channel 624 of valve switch 551 is positioned to receive fluid flow from internal port 614. Either a needle unit or a guide is adapted to engage the transmission means either directly or by means of one or more adapters, such as adapter 630 illustrated in FIG. 13a. The transmission unit is also adapted to engage a sample container, either directly or by means of one or more adapters. Thus, the transmission unit is adapted to receive fluid from the needle unit and to transmit fluid from the needle unit to the container. For example, as illustrated in FIGS. 12a, 12b, 13a and 13b transmission means 550 comprises external receiving port 630, channel 605 and internal port 614. Transmission means 550 further comprises optional external transmitting port 640, optional tube extensions, such as, for example, tube extension 631, and optional external transmitting port cap 632. External receiving port 630 is adapted to engage a port of a guide or the port of an adapter. Fluid received either directly or indirectly at external port 630 then flows through channel 605 to internal port 614.

Valve switch 551 comprises spring 541, actuator 544 and channel 624. When a user presses on actuator 544, as illustrated in FIG. 12b, channel 624 is positioned to receive fluid flow from internal port 614. Fluid received by channel 624 flows to a container through a container adapter.

As illustrated in FIG. 12a, when fluid flow is controlled by gravity, a collecting tube 607 is attached to container adapter 620 by means of adapter 610 and collecting tube 607 moves along with the movement of valve switch 551. In this situation, vent 612 allows air displaced by the fluid entering the collecting tube to flow from collecting tube 607 through optional vent channels 623, 613 and 606.

When actuator 544 is released, fluid flow ceases or bypasses port 614 to flow to external transmitting port 640 and thence to an external receiving port of a subsequent module.

Seals 621 and 611 serve to prevent leakage.

Figure 14:
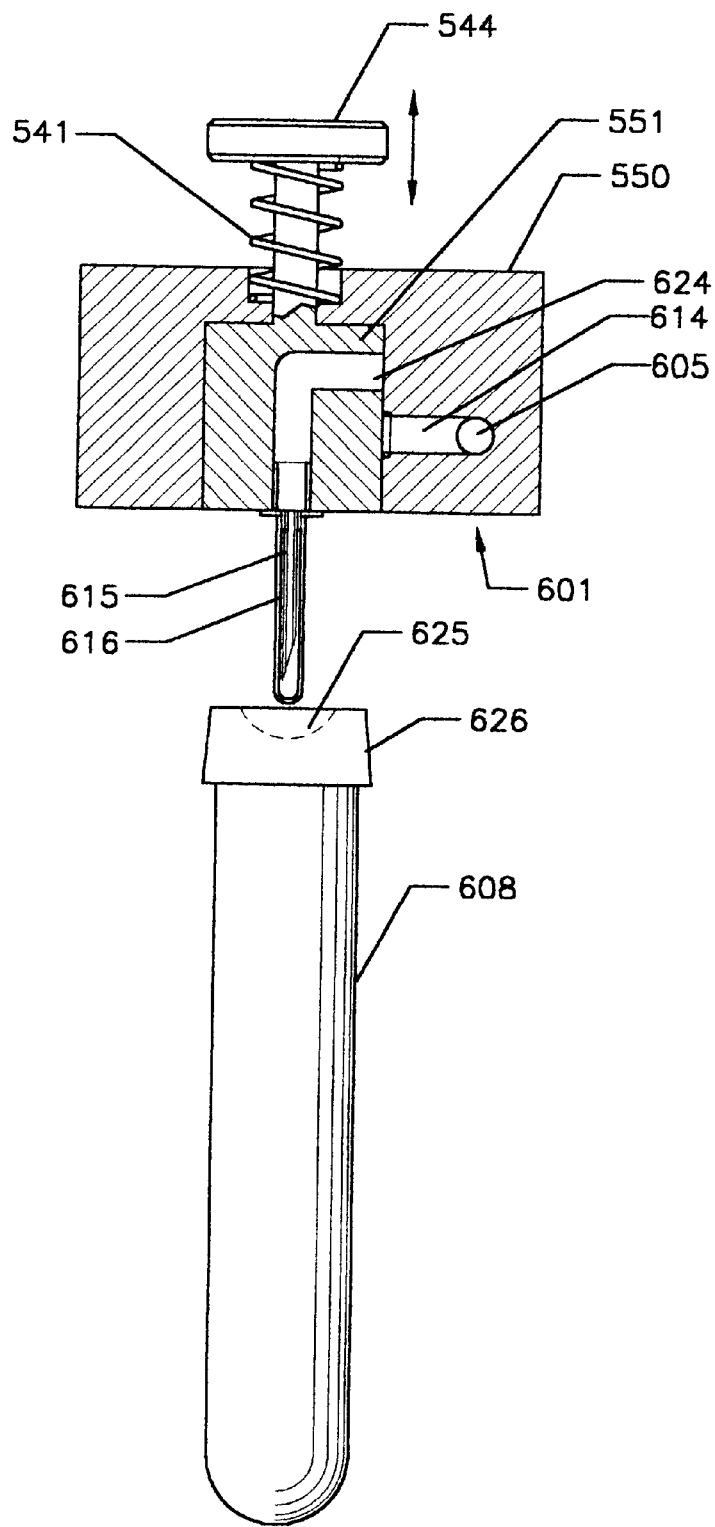
FIG. 14 is another embodiment of a container and assembly of the invention.

As illustrated in FIG. 14, for collection valve module 601, when fluid flow is controlled by a vacuum tube, a vacuum collecting tube 608 is held in a stationary position, such as, for example, by an extension of transmitting unit 550. When a user presses on actuator 544, channel 624 is positioned to receive fluid flow from internal port 614. Fluid received by channel 624 flows to a container through a container adapter. In this situation, the container adapter to which fluid flows from channel 624 comprises a needle such as, for example, a vacutainer needle 615 and sleeve 616. The needle pierces indent 625 in cap 626 and the vacuum tube is filled.

In both the gravity fill scenario and the vacuum tube scenario, a series of modules can be connected together such as in a rigid manifold or a flexible strap to permit a series of tubes to be filled without need for the user to reach for and exchange one tube after another as is currently done in drawing blood using a conventional vacutainer system. An alternative in the vacuum tube scenario is a number of collecting tubes contained in a rigid manifold or a strap can be presented in series to a single valve module.

The foregoing description and accompanying drawings are provided for illustration and example. It is understood that various changes, adaptations and modifications may be made without departing from the spirit of the invention which is limited only by the scope of the claims which follow.

What is claimed is:

1. A needle unit comprising a hollow needle, a hub and a stylet, said hollow needle comprising a lumen, said hollow needle being attached to said hub, said hub comprising a distal end, a proximal end, and a chamber, said needle being attached to said hub at said distal end of said hub, said proximal end comprising an aperture, said stylet having a distal end and a shaft, said distal end of said stylet being broader than said aperture, said aperture comprising cross-sectional dimensions that permit the passage of said shaft, and that prevent the passage of said distal end of said stylet, and that provide a sufficiently snug fit with said stylet to limit leakage of fluid through said aperature.

2. The needle unit of claim 1 wherein said needle is permanently attached to said hub.

3. The needle unit of claim 1 wherein said stylet is a cutting stylet.

4. The needle unit of claim 1 wherein said stylet comprises a recess and said needle is a cutting needle.

5. The needle unit of claim 1 wherein said hub further comprises at least one port, each said port communicating with said chamber.

6. The needle unit of claim 1 wherein said stylet is tapered from the distal end of said sylet to the shaft of said stylet.

* * * * *